United States Patent [19]

Lagana' et al.

[11] Patent Number: 4,500,734
[45] Date of Patent: Feb. 19, 1985

[54] PROCESS FOR THE PRODUCTION OF UREA

[75] Inventors: Vincenzo Lagana', Milan; Virginio Cavallanti, Vailate, both of Italy

[73] Assignee: Snamprogetti S.p.A., Milan, Italy

[21] Appl. No.: 367,792

[22] Filed: Apr. 12, 1982

Related U.S. Application Data

[63] Continuation of Ser. No. 215,168, Dec. 11, 1980, abandoned.

[51] Int. Cl.$^3$ ............................................ C07C 126/02
[52] U.S. Cl. ........................................ 564/72; 564/68; 564/70
[58] Field of Search ............................ 564/72, 68, 70

[56] References Cited

U.S. PATENT DOCUMENTS 3,470,247  9/1969  Guadalupi ............................ 564/72
3,471,558  10/1969  Wentworth et al. ................. 564/72
3,514,484  5/1970  Wentworth ........................... 564/72
3,607,938  9/1971  Braun ................................... 564/70

Primary Examiner—Paul F. Shaver
Attorney, Agent, or Firm—Hedman, Gibson, Costigan & Hoare

[57] ABSTRACT

A process for the production of urea starting from ammonia and carbon dioxide in a $NH_3/CO_2$ molar ratio of from 5/1 to 8/1, comprising the synthesis and decomposition of the ammonium carbamate contained in the solution of urea, in two steps; the first of these provides for ammonia as the stripping agent and the second for carbon dioxide as the stripping agent.

In the process of the invention the synthesis and the decomposition in the first decomposition step are carried out at an equal or substantially equal pressure comprised between 180 and 250 atm., while the decomposition in the second step is carried out at a pressure of from 30 to 50 atm. lower than the pressure in the first step.

1 Claim, 1 Drawing Figure

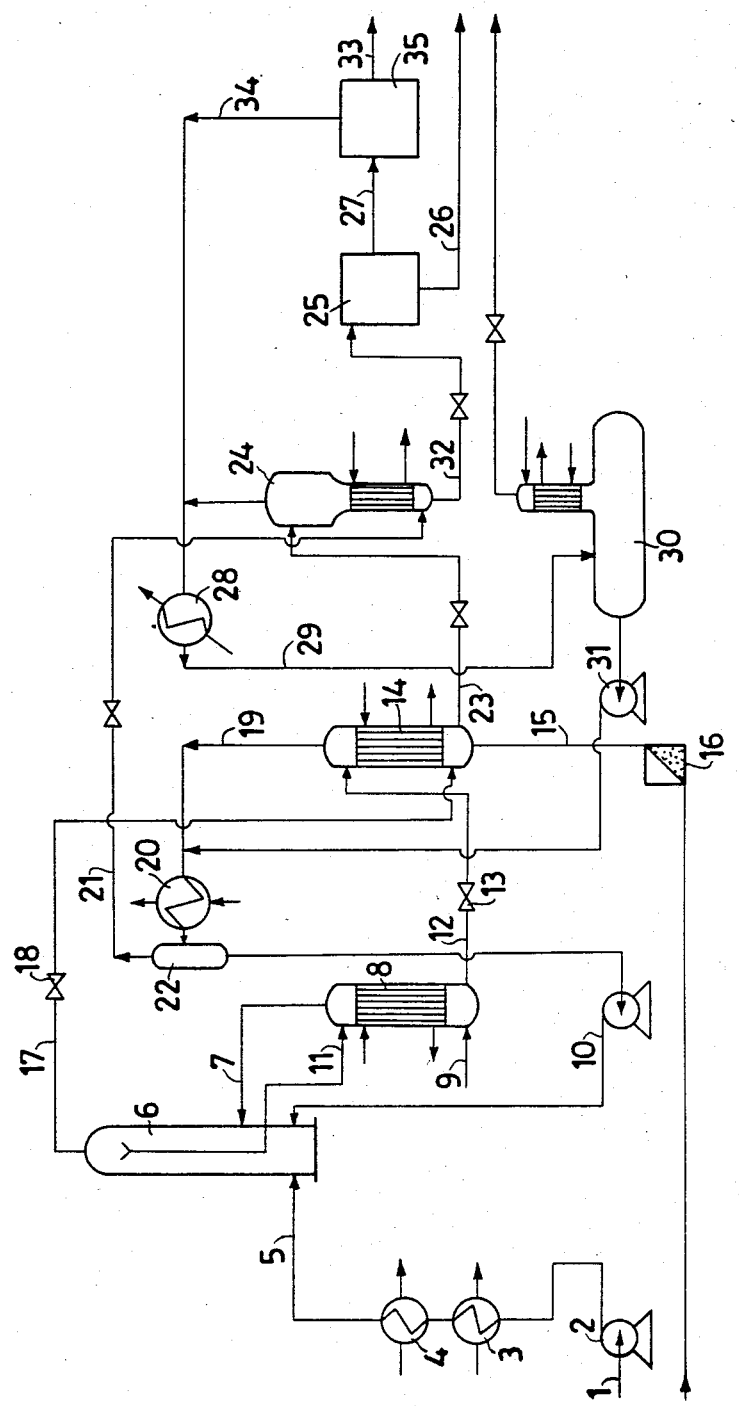

PROCESS FOR THE PRODUCTION OF UREA

This is a continuation of application Ser. No. 215,168 filed Dec. 11, 1980, now abandoned.

The present invention relates to a process for the production of urea. The prior art contains many such processes, which can be subdivided into the following categories:

(a) processes in which the ammonium carbamate contained in the solution of urea coming from the synthesis zone is decomposed thermally in more than two steps all at a pressure lower than the synthesis pressure;

(b) processes in which the ammonium carbamate is essentially decomposed in a single step substantially at the same pressure as the synthesis pressure, using as stripping agents decomposition products of said ammonium carbamate: gaseous ammonia and carbon dioxide;

(c) processes in which the ammonium carbamate is decomposed in two steps, substantially at the same pressure as the synthesis pressure, using ammonia as the stripping agent in the first step and inert gases or carbon dioxide for the same purpose in the second step.

From among these known processes, there is one described in the U.S. Pat. No. 3,607,938 according to which the decomposition of the ammonium carbamate can be effected in two steps, the first of which includes ammonia among the stripping agents and employs the same pressure as the synthesis pressure and the second of which includes carbon dioxide among the stripping agents and employs a pressure lower than the synthesis pressure. It should be noted that of all the previously described processes particular interest might seem to attach to the one providing for the decomposition of the carbamate in the first step in the presence of ammonia and in the second step in the presence of carbon dioxide, the second stage also serving as a stage for the removal of the ammonia dissolved in the solution of urea, both steps being at the same pressure as that of the urea synthesis reactor. In theory, this last mentioned process can employ very high pressures, in that the two-step decomposition with the said stripping agents allows efficient removal of the carbamate and dissolved ammonia, despite the high pressure. However, it has been noted that at high pressures in the decomposition step with carbon dioxide, a strong corrosion is caused both by the high temperature used to decompose the residual carbamate and by the carbon dioxide itself, which is, even at conventional temperatures, extremely corrosive.

The problem of corrosion is solved in the aforesaid U.S. Pat. No. 3,607,938 by using carbon dioxide as stripping agent in the second decomposer unit, together with a part of the decomposition products recycled from the head of the stripper in order to dilute the carbon dioxide in a larger mass of ammonia and above all by using relatively low synthesis and decomposition pressures, of the order of magnitude of 135 atm. as indicated in the example given herein.

It has now surprisingly been found that it is possible to decompose the ammonium carbamate in the second stripper with carbon dioxide, thus on the one hand avoiding the phenomena of corrosion and, on the other hand, effecting the synthesis at high pressures with the resulting advantage of high yields.

The process according to the present invention provides for the synthesis to be performed at a pressure of from 180 to 250 atm, starting from ammonia and carbon dioxide in a $NH_3/CO_2$ polar ratio of from 5/1 to 8/1 in a synthesis zone, the discharge of the solution obtained out of the synthesis zone into a first decomposition zone for decomposition of the ammonium carbamate where the excess ammonia used in the synthesis zone is used as stripping agent. The first decomposition zone is operated at a pressure equal or substantially equal to that of the synthesis zone, the separation in said first decomposition zone of a solution of urea containing a quantity of carbamate of from 5% to 25%, and of a gaseous phase consisting of the decomposition products of the ammonium carbamate as well as of a quantity of ammonia in excess over the stoichiometric quantity necessary for the ammonium carbamate comprised between 50% and 90% of the total throughput of gas. The feeding of the solution of urea from the first decomposition zone is to a second decomposition zone operating at a pressure 30 to 50 atm lower than that of the first zone, the stripper in said second decomposition zone being carbon dioxide.

Temperatures in the first decomposition zone are regulated in such a way as to respect the aforesaid conditions for the total residual carbamate in the solution of urea and for the total excess ammonia in the gaseous phase which is recycled without condensation directly to the urea synthesis zone, the temperatures of the first decomposition zone are maintained in the range 180°–215° C.

The temperatures in the second decomposition zone are maintained in the range 160°–210° C.

The decomposition products and the ammonia which are separated from the solution of urea in the second decomposition zone are condensed at a pressure substantially similar to that of said second decomposition zone and the condensate pumped and recycled to the synthesis zone.

The process according to the present invention will now be made clearer with reference to the attached FIGURE which represents a preferred but not limiting embodiment thereof.

The liquid ammonia 1 is pumped by the pump 2 and, after cooling in 3 and 4, is fed through the conduit 5 to the urea synthesis reactor 6, through the line 7, the decomposition products and excess ammonia coming from the first decomposer unit 8, to which, through 9, air is also fed in order to cause passivation of the first decomposition unit 8 and the reactor 6. The condensate from the second decomposition step is fed to the reactor 6 through the conduit 10.

The solution of urea, which contains the nonconverted ammonium carbamate and the excess ammonia is fed, through the conduit 11, to the said first decomposer unit, from which is discharged, through the conduit 12, a solution of urea containing the carbamate not decomposed in 8 and the excess of ammonia not removed in 8.

The solution discharged by the first decomposer unit is expanded in the valve 13 with a reduction of 30–50 atm and fed to the second decomposer unit 14, wherein it is stripped with carbon dioxide fed from 15 after being compressed by the compressor 16.

The second decomposer unit 14 is also fed with the gaseous stream 17, expanded to the pressure of said second decomposer unit through the valve 18, coming from the head of the reactor 6 and consisting of $NH_3$, $CO_2$, oxygen, nitrogen and any other inert gases present in the feed streams.

The vapours stripped in the second decomposer unit 14, the $CO_2$ stripper and the inert matter are discharged through the line 19 and then condensed in the condenser 20, the liquid phase 10 being separated from the gaseous phase 21 in the separator 22. The solution of urea 23 leaving the second decomposer unit 14 is then expanded and given conventional distillation treatments in 24, obtaining a solution 32 which is concentrated in vacuo in 25, obtaining a urea melt 26 which is sent to a prilling or granulation step, and the condensates 27.

The condensates 27 from the vacuum concentration section 25 are sent to the treatment section 35, from which is obtained discharge waters 33 and an ammonical solution which is recycled through the line 34 to the condenser 28.

The ammoniacal vapour obtained from the head of 24 is condensed in 28 sent through the line 29 to the tank 30 and recycled to the condenser 20 by the pump 31. An example of a practical embodiment is now provided, the purpose of which is to illustrate the results obtained with the process according to the invention, though the invention is not confined to said example.

EXAMPLE

For an output of 1500 tons/day, the flow diagram attached is applied. The characteristics of the more significant throughputs are as follows:

| LINE DESCRP. | 1 $NH_3$ LIQ | | 5 $NH_3$ LIQ | | 15 $CO_2$ GAS | | 11 LIQUID | | 12 LIQUID | | 23 LIQUID | |
|---|---|---|---|---|---|---|---|---|---|---|---|---|
| T (°C.) | 15 | | 120 | | 160 | | 190 | | 200 | | 180 | |
| P (atm) | 10 | | 200 | | 150 | | 200 | | 200 | | 150 | |
| $NH_3$ (kg/h) | 35417 | 100 | 35417 | 100 | | | 85877 | 43.05 | 43603 | 30 | 7543 | 7 |
| $CO_2$ (kg/h) | | | | | 45831 | 100 | 16954 | 8.5 | 10174 | 7 | 9699 | 9 |
| UREA (kg/h) | | | | | | | 62499 | 31.33 | 62499 | 43 | 62499 | 58 |
| $H_2O$ (kg/h) | | | | | | | 34153 | 17.12 | 29070 | 20 | 28016 | 26 |
| TOTAL | 35417 | (%) | 35417 | % | 45831 | % | 199483 | % | 145346 | % | 107757 | % |

| LINE DESCRIP. | 32 LIQUID | | 26 UREA MELT | | 29 LIQUID | | 10 LIQUID | | 34 LIQUID | |
|---|---|---|---|---|---|---|---|---|---|---|
| T (°C.) | 140 | | 140 | | 70 | | 170 | | 40 | |
| P (atm) | 4.5 | | 0.03 | | 4.5 | | 200 | | 4.5 | |
| $NH_3$ (kg/h) | 1731 | 2 | | | 7543 | 28.4 | 43603 | 39.66 | 1731 | 32.58 |
| $CO_2$ (kg/h) | 694 | 0.8 | | | 9699 | 36.6 | 56006 | 50.95 | 694 | 13.06 |
| UREA (kg/h) | 62499 | 72.2 | 62499 | 100 | | | | | | |
| $H_2O$ (kg/h) | 21639 | 25 | | | 9266 | 35 | 10320 | 9.39 | 2889 | 54.36 |
| TOTAL | 86563 | % | 62499 | % | 26508 | % | 109929 | % | 5314 | % |

N/C = 5
H/C = 0.6
$\eta$ = 0.73

We claim:

1. A process for the production of urea starting from ammonia and carbon dioxide in a $NH_3/CO_2$ ratio of from 5/1 to 8/1 comprising the synthesis and decomposition of the ammonium carbamate contained in the solution of urea in two steps, the first providing for ammonia and the second for carbon dioxide as strippers, characterized by the fact that the synthesis and decomposition in the first decomposition step are carried out at a pressure equal or substantially equal and comprised between 180 and 250 atm, and where from the first decomposition zone a solution of urea containing from 5 to 25% of carbamate is discharged with a gaseous phase containing a quantity of ammonia in excess with regard to the stoichiometric quantity for forming ammonium carbamate, said excess ammonia being from 50% and 90% of the total gas throughput, while the decomposition in the second step is carried out at a pressure 30–50 atm. lower than the pressure in the first step and the gases leaving the reactor being fed to the bottom of the decomposer in the second decomposition step.

* * * * *